US011725927B2

United States Patent
Frisken

(10) Patent No.: US 11,725,927 B2
(45) Date of Patent: Aug. 15, 2023

(54) OPTICAL COHERENCE TOMOGRAPHY WITH DISPERSED STRUCTURED ILLUMINATION

(71) Applicant: Cylite Pty Ltd, Notting Hill (AU)

(72) Inventor: Steven James Frisken, Vaucluse (AU)

(73) Assignee: Cylite Pty Ltd, Notting Hill (AU)

( * ) Notice: Subject to any disclaimer, the term of this patent is extended or adjusted under 35 U.S.C. 154(b) by 0 days.

(21) Appl. No.: 17/522,245

(22) Filed: Nov. 9, 2021

(65) Prior Publication Data

US 2022/0065616 A1   Mar. 3, 2022

Related U.S. Application Data

(62) Division of application No. 16/560,970, filed on Sep. 4, 2019, now Pat. No. 11,193,752.

(30) Foreign Application Priority Data

Sep. 5, 2018   (AU) ................. 2018903308

(51) Int. Cl.
*G01B 9/02* (2022.01)
*G01B 9/02091* (2022.01)
(Continued)

(52) U.S. Cl.
CPC ..... *G01B 9/02091* (2013.01); *G01B 9/02063* (2013.01); *G01B 9/02084* (2013.01);
(Continued)

(58) Field of Classification Search
CPC ............ G01B 9/02008; G01B 9/02091; G01B 9/02063; G01B 9/02084; A61B 5/0066; A61B 5/7257; G01N 21/4795
See application file for complete search history.

(56) References Cited

U.S. PATENT DOCUMENTS 8,446,593 B1   5/2013 Ellerbee
2008/0192236 A1   8/2008 Smith et al.
(Continued)

FOREIGN PATENT DOCUMENTS

WO   2018000036 A1   1/2018

OTHER PUBLICATIONS

Lian Duan, Hee Yoon Lee, Gary Lee, Monica Agrawal, Gennifer T. Smith, Audrey K. Ellerbee, "Single-shot speckle noise reduction by interleaved optical coherence tomography," J. Biomed. Opt. 19(12) 120501 (Dec. 8, 2014) (Year: 2014).*
(Continued)

*Primary Examiner* — Tarifur R Chowdhury
*Assistant Examiner* — Jonathon Cook
(74) *Attorney, Agent, or Firm* — Mattingly & Malur, PC

(57) ABSTRACT

Apparatus and methods are presented for enhancing the acquisition speed or performance of Fourier domain optical coherence tomography. In preferred embodiments a plurality of wavelength combs containing interleaved selections of wavelengths from a multi-wavelength optical source are generated and projected onto a sample. In certain embodiments the wavelength combs are projected simultaneously onto a plurality of regions of the sample, while in other embodiments the wavelength combs are projected sequentially onto the sample. Light in the wavelength combs reflected or scattered from the sample is detected in a single frame of a sensor array, and the detected light processed to obtain a tomographic profile of the sample. In preferred embodiments the wavelength comb generator comprises a wavelength interleaver in the form of a retro-reflective prism array for imparting different displacements to different selections of wavelengths from the optical source.

15 Claims, 8 Drawing Sheets

(51) Int. Cl.
G01B 9/02055 (2022.01)
G01N 21/47 (2006.01)
A61B 5/00 (2006.01)

(52) U.S. Cl.
CPC ........... A61B 5/0066 (2013.01); A61B 5/7257 (2013.01); G01N 21/4795 (2013.01)

(56) References Cited

U.S. PATENT DOCUMENTS

| | | | |
|---|---|---|---|
| 2011/0235045 A1* | 9/2011 | Koerner | G02B 21/0056 356/451 |
| 2012/0127472 A1 | 5/2012 | Alphonse | |
| 2014/0028974 A1 | 1/2014 | Tumlinson | |
| 2015/0077760 A1* | 3/2015 | Koerner | G01B 9/02027 356/496 |
| 2016/0157721 A1 | 6/2016 | Vakoc et al. | |
| 2016/0345820 A1 | 12/2016 | Frisken et al. | |
| 2017/0363415 A1 | 12/2017 | Frisken | |

OTHER PUBLICATIONS

Lian Duan, Tahereh Marvdashti, and Audrey K. Ellerbee, "Polarization-sensitive interleaved optical coherence tomography," Opt. Express 23, 13693-13703 (2015) (Year: 2015).*

Hrebesh Molly Subhash, "Full-Field and Single-Shot Full-Field Optical Coherence Tomography: A Novel Technique for Biomedical Imaging Applications", Advances in Optical Technologies, vol. 2012, Article ID 435408, 26 pages, 2012 (Year: 2012).*

Bonin et al 'In vivo Fourier-domain full-field OCT of the human retina with 1 5 million A-lines/s', Optics Letters 35(20), 3432-3434 (2010).

Pfäffle et al. 'Reduction of frame rate in full-field swept-source optical coherence tomography by numerical motion correciton'. Biomedical Optics Express 8(3), 1499-1511 (2017).

Hillmann et al 'Off-axis reference beam for full-field swept-source OCT and holoscopy', Optics Express 25(22), 27770-27784(2017).

Siddiqui et al 'Optical-domain subsampling for data efficient depth ranging in Fourier-domain optical coherence tomography' Optics Express 20(16), 17938-17951 (2021).

Lee et al 'High speed parallel spectral-domain OCT using spectrally encoded line-field illumination' Applied Physics Letters 112, 041102(2018).

Nakamura et al 'High-speed three-dimensional human retinal imaging by line-field spectral domain optical coherence tomography', Optics Express 15(12), 7103-7116 (2007).

Liu et al 'Computational optical coherence tomography', Biomedical Optics Express 8(3), 1549-1574.

Holmes 'Theory & applications of multi beam OCT', Proc SPIE 7139, 713908-1-713908-7 (2008).

Siddiqui, M. 'Optical domain subsampling for data-efficient optical coherence tomography (OCT)', M.Sc.thesis, Massachusetts Institute of Technology (Jun. 2013).

Siddiqui et al 'Simultaneous high-speed and long-range imaging with optically subsampled OCT', Proc SPIE 9697, 9697ON (2016).

* cited by examiner

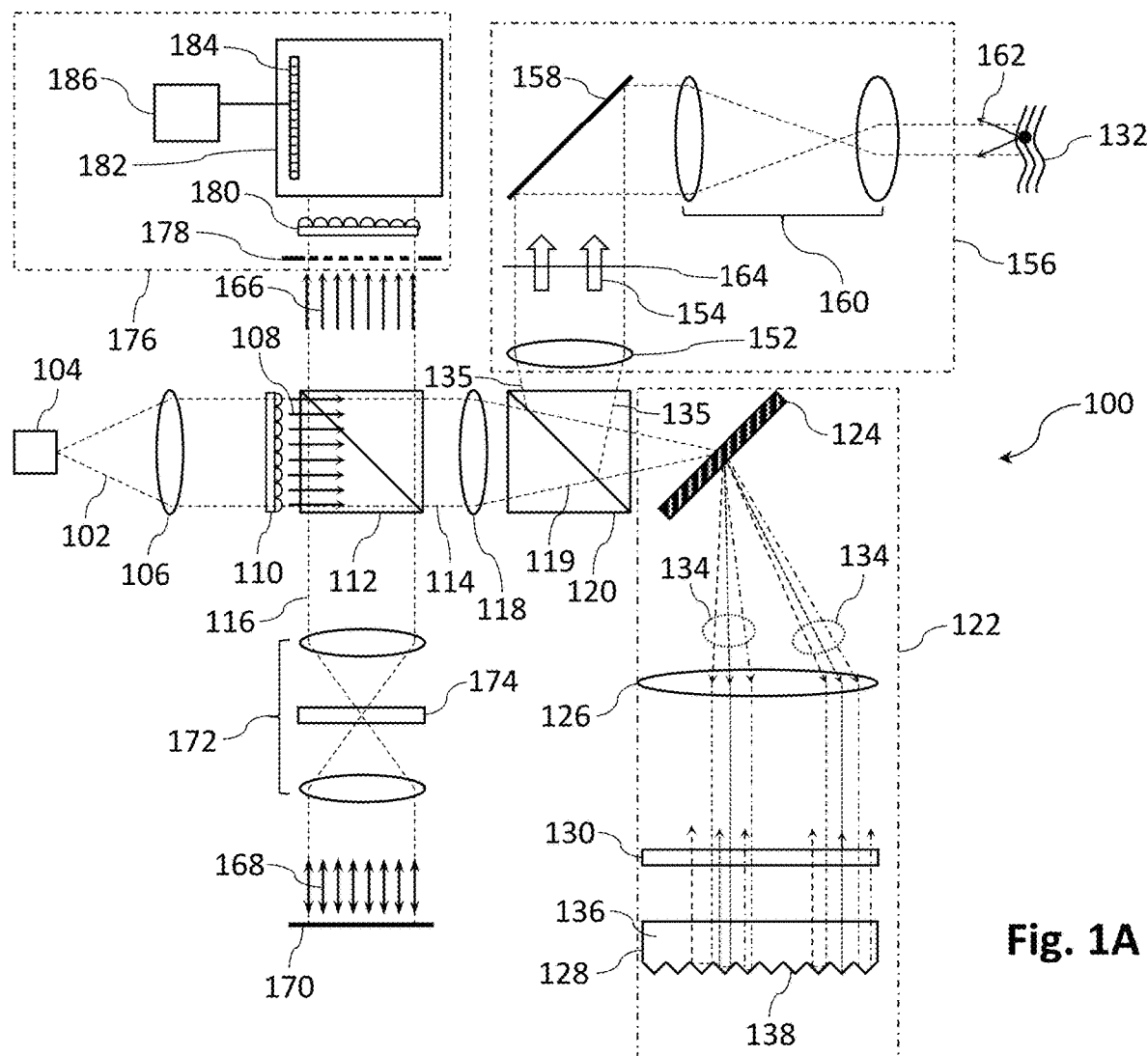
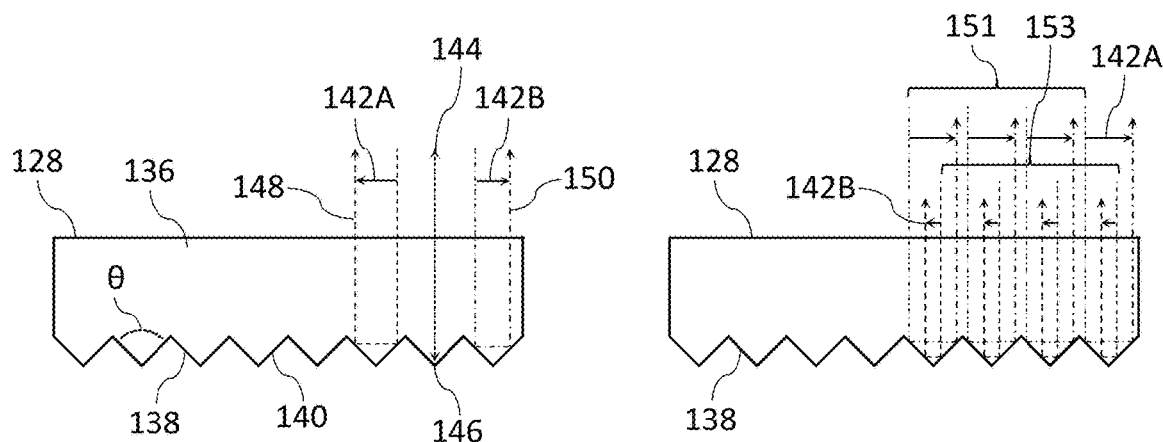
Fig. 1A
Fig. 1B
Fig. 1C

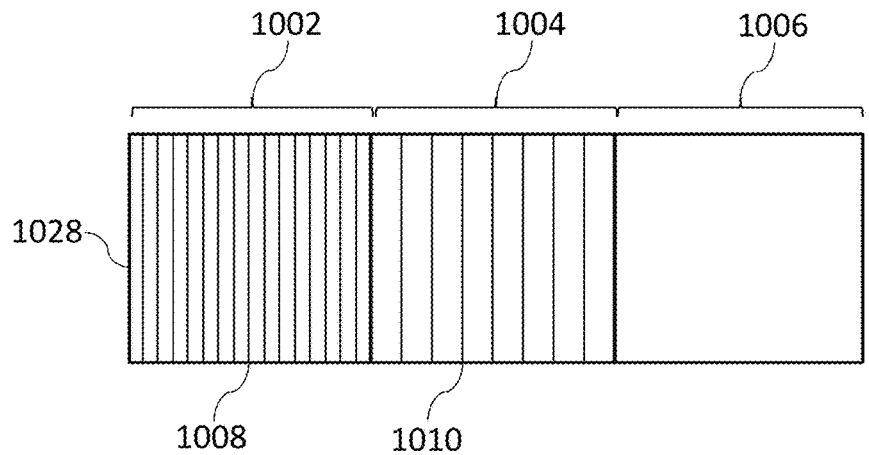
Fig. 10A
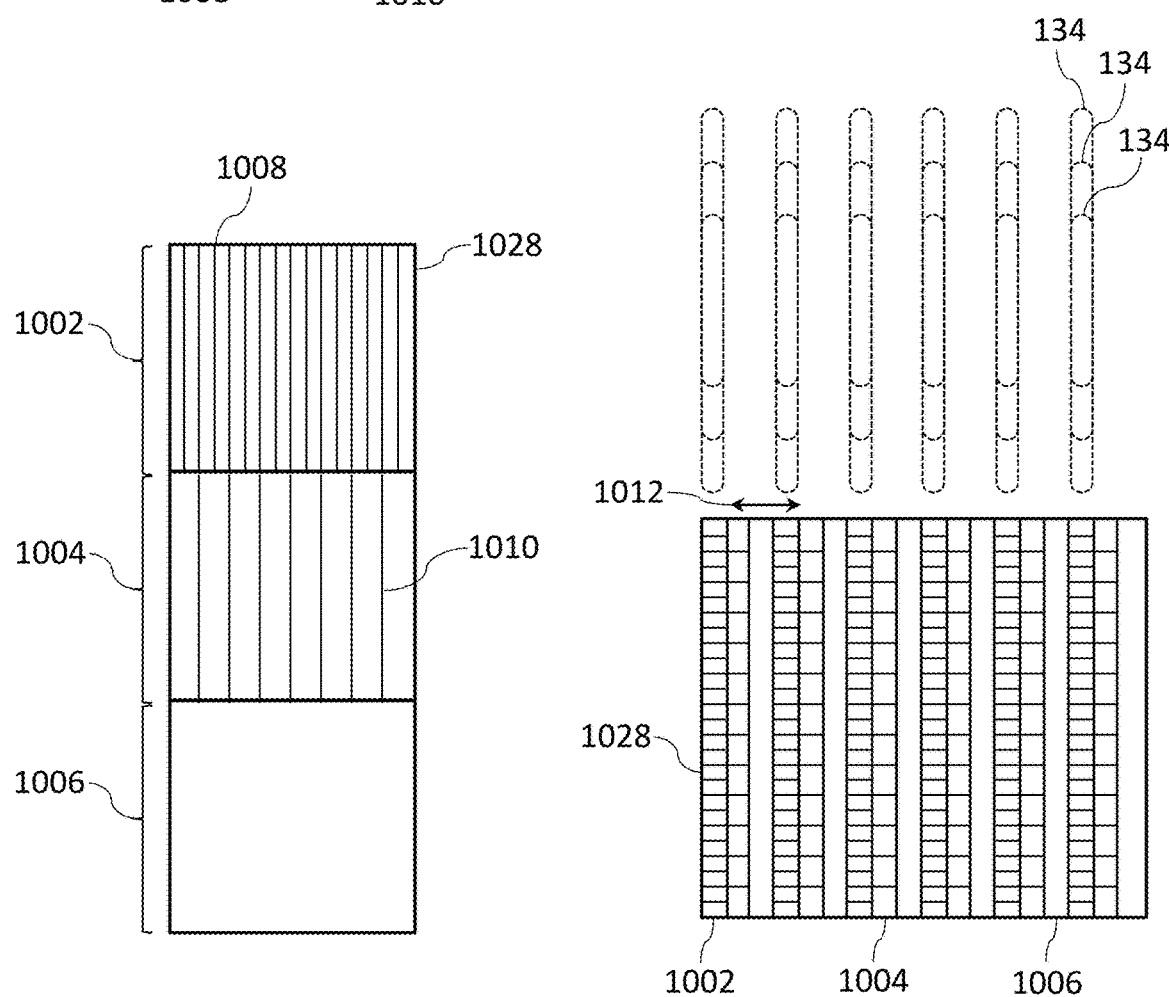
Fig. 10B                    Fig. 10C

OPTICAL COHERENCE TOMOGRAPHY WITH DISPERSED STRUCTURED ILLUMINATION

RELATED APPLICATIONS

The present application claims priority from Australian Provisional Patent Application No 2018903308 filed on 5 Sep. 2018, the contents of which are incorporated herein by reference.

FIELD OF THE INVENTION

The invention relates to apparatus and methods for optical coherence tomography (OCT), in particular for enhancing the acquisition speed or performance of Fourier domain OCT. However it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Optical coherence tomography (OCT) is a widely used interferometric technique for non-invasive depth-resolved study of biological samples, including in-vivo tissue such as the human eye, using information contained within the amplitude and phase of light reflected or scattered from various structures in the sample. The earliest OCT systems, developed in the early 1990s, were 'time domain' systems that used a time-varying path length difference between sample and reference beams to reconstruct the reflection profile of a sample in the depth dimension. Time domain OCT (TD-OCT) has been largely superseded by Fourier domain techniques that provide significantly better sensitivity and imaging speed. The speed improvement is essentially obtained by parallelising the detection of depth information and is particularly important for minimising motion artefacts when studying in-vivo samples. Fourier domain OCT (FD-OCT) appears in two forms: swept source OCT (SS-OCT) in which the spectrum of the interference signal is recorded by a photodetector as the wavelength of the light source is scanned; and spectral domain OCT (SD-OCT) in which the spectrum of the interference signal is dispersed onto a detector array. In both cases phase and amplitude information from various layers in the sample are encoded in the interference spectrum and the depth-resolved reflectivity profile can be extracted by Fourier transformation.

Many groups over several years have pursued various strategies for further enhancing the acquisition speed of OCT to extend the limits in terms of wide field, high resolution (lateral or depth) or temporally resolved imaging, for example to increase the volume over which motion artefact-free data can be acquired or to increase the temporal sampling rate for angio-imaging or surgical applications. Several of these strategies involve spatial parallelisation, either laterally or in the depth dimension, to probe multiple sample areas simultaneously rather than sequentially. For example published US patent application No 2008/0192236 A1 entitled 'Optical interference apparatus' describes a multi-beam technique for obtaining interferograms simultaneously from a number of different focal depths in a sample. A lateral parallelisation scheme for SS-OCT is described in Bonin et al 'In vivo Fourier-domain full-field OCT of the human retina with 1.5 million A-lines/s', *Optics Letters* 35(20), 3432 (2010), although this approach is vulnerable to motion artefacts because the A-scan acquisition time, given by the product of the frame period and the number of k-values, is relatively slow. Other SS-OCT schemes with laterally parallelised detection have been disclosed in published US patent application No 2017/0363415 A1 entitled 'Multichannel optical receivers', Pfaffle et al 'Reduction of frame rate in full-field swept-source optical coherence tomography by numerical motion correction', *Biomedical Optics Express* 8(3), 1499 (2017) and Hillmann et al 'Off-axis reference beam for full-field swept-source OCT and holoscopy', *Optics Express* 25(22), 27770 (2017).

Lateral parallelisation is more complicated with SD-OCT than with SS-OCT because of the need to disperse the interference signal across a plurality of pixels of a two-dimensional (2-D) detector array. Published US patent application No 2014/0028974 A1 entitled 'Line-field holoscopy' describes a line-field approach, i.e. simultaneous B-scan acquisition in which the interference signals from various points along an illuminated line on a sample are dispersed onto separate columns of pixels of a 2-D array. However for full three-dimensional (3-D) imaging, i.e. C-scan acquisition, the illuminated line has to be scanned in the orthogonal direction and the series of B-scans stitched together, which can be difficult to achieve with phase accuracy especially in-vivo. Published US patent application No 2016/0345820 A1 entitled 'High resolution 3-D spectral domain optical imaging apparatus and method' discloses a scheme in which the interference signal from an extended sample area is sampled with a 2-D lenslet array and the resulting grid of beamlets dispersed onto separate groups of pixels of a 2-D detector array. Lateral scanning may still be required to image larger areas of the sample, but the accuracy with which frames are stitched together is improved by ensuring that the areas imaged in different frames are partially overlapping. It would be advantageous to sample the interference signal with a tighter 2-D grid, but the number of spectrally resolved points would need to be reduced to allow the interference signals to be projected unambiguously onto the 2-D detector array, i.e. dispersed onto non-overlapping groups of pixels. A drop-off in sensitivity would then occur over an equivalently reduced distance, determined by the Nyquist sampling theory, and it is then difficult to obtain a good quality scan as the sample-to-instrument distance needs to be precisely controlled.

Another approach to increasing FD-OCT acquisition speed is optical subsampling, i.e. reducing the number of k-values at each image point while substantially maintaining the overall wavelength range, to increase the A-scan rate without sacrificing depth resolution. Put simply, optical subsampling reduces the number of wavelength samples that need to be read out and processed for each image point. Generally this can be achieved by exposing the sample to a comb of wavelengths selected from the bandwidth emitted by an optical source. Optical subsampling schemes for either SS-OCT or SD-OCT have been described for example in Siddiqui et al 'Optical-domain subsampling for data efficient depth ranging in Fourier-domain optical coherence tomography' *Optics Express* 20(16), 17938 (2012), U.S. Pat. No. 8,446,593 entitled 'Optical coherence tomography system and method therefore' and Lee et al 'High speed parallel spectral-domain OCT using spectrally encoded line-field illumination' *Applied Physics Letters* 112, 041102 (2018). However these schemes require either scanning mirrors or expensive electronics and optics to generate the wavelength comb, making them less attractive for clinical applications requiring robust and low-cost operation.

The reduction in the number of k-values per image point also reduces the volume of data that needs to be processed, but comes at the expense of reduced unambiguous sampling depth, i.e. the depth range before the image starts to wrap around on itself. In the context of ocular imaging this may complicate imaging of the anterior segment, i.e. cornea, aqueous humour and lens, but is less likely to affect corneal imaging where there is a natural depth associated with the corneal thickness, or retinal imaging where various choices on sampling depth can be made depending on the application. For these and other in-vivo applications consideration needs to be taken for the impact of motion and the sampling time following a blink, which for patient comfort should only be a few seconds at most. In existing SD-OCT systems a reduction in the number of k-values (i.e. wavelength samples) has a corresponding reduction in the drop-off of signal depth over a distance that is limited by the separation of the k-values and the resolving power of the spectrometer. It would be highly advantageous to have a much faster sampling SD-OCT system with reduced k-values per A-scan, without sacrificing sensitivity or making the system sensitive to the relative locations of the sample and the instrument.

Unless the context clearly requires otherwise, throughout the description and the claims the words 'comprising', 'comprises' and the like are to be construed in an inclusive sense as opposed to an exclusive or exhaustive sense. That is, they are to be construed in the sense of 'including, but not limited to'.

OBJECT OF THE INVENTION

It is an object of the present invention to overcome or ameliorate at least one of the limitations of the prior art, or to provide a useful alternative. It is an object of the present invention in a preferred form to provide a Fourier domain OCT apparatus with enhanced acquisition speed.

SUMMARY OF THE INVENTION

According to a first aspect of the present invention there is provided an imaging apparatus comprising:

a wavelength dispersive element for angularly dispersing or recombining a plurality of wavelengths emitted from an optical source;

a first focusing element for focusing the angularly dispersed plurality of wavelengths at least in the direction of the dispersion;

a wavelength interleaver for imparting a first displacement to a first selection of wavelengths from said plurality of wavelengths and a second displacement to a second selection of wavelengths from said plurality of wavelengths, said first and second selections of wavelengths being interleaved;

a relay system for forming first and second wavelength combs from said first and second selections of wavelengths and for projecting said first and second wavelength combs onto a sample; and a detection system for detecting, in a single frame of a sensor array, light in said first and second wavelength combs reflected or scattered from said sample.

In certain embodiments the first focusing element comprises a lens positioned between the wavelength dispersive element and the wavelength interleaver. In other embodiments the wavelength dispersive element and the first focusing element are a single element. In certain embodiments the single element comprises a chirped grating.

Preferably, the wavelength interleaver comprises an array of reflective elements. More preferably, the wavelength interleaver comprises an array of retro-reflective elements, such that the wavelength dispersive element recombines the plurality of wavelengths so as to produce, from the first and second selections of wavelengths, first and second wavelength combs propagating at first and second angles. In preferred embodiments the retro-reflective elements comprise retro-reflective prisms.

Preferably, the relay system comprises a second focusing element for focusing the first and second wavelength combs so as to produce a laterally separated array of wavelength combs.

In certain embodiments the relay system is configured to project the first and second wavelength combs simultaneously onto laterally separated regions of the sample, and the sensor array is a two-dimensional sensor array. The apparatus preferably comprises a spatial sampling element for splitting a beam emitted from the optical source into multiple beamlets, such that the relay system projects multiple sets of the first and second wavelength combs onto a plurality of regions of the sample. Preferably, the projected multiple sets of first and second wavelength combs form a two-dimensional illumination grid on the sample. In preferred embodiments the spatial sampling element comprises a two-dimensional lenslet array. In certain embodiments the spatial sampling element is oriented with respect to the wavelength dispersive element such that the two-dimensional illumination grid provides substantially contiguous coverage of an area of the sample.

Preferably, the detection system comprises an aperture array for spatially filtering light in the first and second wavelength combs reflected or scattered from the sample.

In certain embodiments the relay system comprises a wavelength comb selector for projecting the first and second wavelength combs onto the sample sequentially. The wavelength comb selector may comprise an adjustable beam steering element and an aperture. In certain embodiments the relay system is configured to project the first and second wavelength combs onto the same region of the sample.

In preferred embodiments the apparatus comprises an optical splitter for splitting light from the optical source into a sample beam and a reference beam, and for recombining the sample and reference beams after the sample beam has interacted with the sample, such that the detection system is able to obtain a tomographic profile of the sample.

According to a second aspect of the present invention there is provided a method for imaging a sample, said method comprising the steps of:

angularly dispersing or recombining a plurality of wavelengths emitted from an optical source;

focusing the angularly dispersed plurality of wavelengths at least in the direction of the dispersion;

imparting a first displacement to a first selection of wavelengths from said plurality of wavelengths and a second displacement to a second selection of wavelengths from said plurality of wavelengths, said first and second selections of wavelengths being interleaved;

forming first and second wavelength combs from said first and second selections of wavelengths;

projecting said first and second wavelength combs onto a sample; and detecting, in a single frame of a sensor array, light in said first and second wavelength combs reflected or scattered from said sample.

According to a third aspect of the present invention there is provided an optical coherence tomography apparatus comprising:

an optical source for emitting a plurality of wavelengths;
a wavelength comb generator for generating two or more wavelength combs containing interleaved selections of wavelengths from said plurality of wavelengths;
a relay system for projecting said two or more wavelength combs onto a sample;
a detection system for detecting, in a single frame of a two-dimensional sensor array, light in said two or more wavelength combs reflected or scattered from said sample; and
an optical splitter for splitting light from said optical source into a sample beam and a reference beam, and for recombining said sample and reference beams after said sample beam has interacted with said sample, such that said detection system is able to obtain a tomographic profile of said sample.

According to a fourth aspect of the present invention there is provided a method for obtaining a tomographic profile of a sample, said method comprising the steps of:

splitting light comprising a plurality of wavelengths into a sample beam and a reference beam;
generating two or more wavelength combs containing interleaved selections of wavelengths from said plurality of wavelengths;
projecting said two or more wavelength combs onto a sample;
recombining said sample beam and said reference beam after said sample beam has interacted with said sample;
detecting, in a single frame of a two-dimensional sensor array, light in said two or more wavelength combs reflected or scattered from said sample; and
processing the detected light to obtain a tomographic profile of said sample.

According to a fifth aspect of the present invention there is provided an imaging apparatus comprising:

a wavelength dispersive element for angularly dispersing or recombining a plurality of wavelengths emitted from an optical source;
a focusing element for focusing the angularly dispersed plurality of wavelengths at least in the direction of the dispersion;
a wavelength interleaver for imparting a first displacement to a first selection of wavelengths from said plurality of wavelengths and a second displacement to a second selection of wavelengths from said plurality of wavelengths, said first and second selections of wavelengths being interleaved;
a relay system for forming first and second wavelength combs from said first and second selections of wavelengths and for projecting said first and second wavelength combs simultaneously onto a sample; and a detection system for detecting, in a single frame of a two-dimensional sensor array, light in said first and second wavelength combs reflected or scattered from said sample.

According to a sixth aspect of the present invention there is provided a method for imaging a sample, said method comprising the steps of:

angularly dispersing or recombining a plurality of wavelengths emitted from an optical source;
focusing the angularly dispersed plurality of wavelengths at least in the direction of the dispersion;
imparting a first displacement to a first selection of wavelengths from said plurality of wavelengths and a second displacement to a second selection of wavelengths from said plurality of wavelengths, said first and second selections of wavelengths being interleaved;
forming first and second wavelength combs from said first and second selections of wavelengths;
projecting said first and second wavelength combs simultaneously onto a sample; and
detecting, in a single frame of a two-dimensional sensor array, light in said first and second wavelength combs reflected or scattered from said sample.

According to a seventh aspect of the present invention there is provided an imaging apparatus comprising:

a wavelength dispersive element for angularly dispersing or recombining a plurality of wavelengths emitted from an optical source;
a focusing element for focusing the angularly dispersed plurality of wavelengths at least in the direction of the dispersion;
a wavelength interleaver for imparting a first displacement to a first selection of wavelengths from said plurality of wavelengths and a second displacement to a second selection of wavelengths from said plurality of wavelengths, said first and second selections of wavelengths being interleaved;
a relay system for forming first and second wavelength combs from said first and second selections of wavelengths and for projecting said first and second wavelength combs sequentially onto a sample; and
a detection system for detecting, in a single frame of a sensor array, light in said first and second wavelength combs reflected or scattered from said sample.

According to an eighth aspect of the present invention there is provided a method for imaging a sample, said method comprising the steps of:

angularly dispersing or recombining a plurality of wavelengths emitted from an optical source;
focusing the angularly dispersed plurality of wavelengths at least in the direction of the dispersion;
imparting a first displacement to a first selection of wavelengths from said plurality of wavelengths and a second displacement to a second selection of wavelengths from said plurality of wavelengths, said first and second selections of wavelengths being interleaved;
forming first and second wavelength combs from said first and second selections of wavelengths;
projecting said first and second wavelength combs sequentially onto a sample; and
detecting, in a single frame of a sensor array, light in said first and second wavelength combs reflected or scattered from said sample.

According to a ninth aspect of the present invention there is provided a method for reconstructing a synthetic wavefront across an area of a sample, said method comprising the steps of:

(i) simultaneously detecting a plurality of signals comprising light in a plurality of wavelength combs reflected or scattered from a plurality of locations on a sample, wherein said plurality of wavelength combs comprise interleaved selections of wavelengths; and
(ii) scaling the relative phase of said plurality of signals to account for the different wavelengths in said plurality of wavelength combs, to create a synthetic wavefront across said plurality of locations on said sample.

Preferably, the scaling also accounts for differences between the distances of the plurality of locations from a zero point delay. The plurality of locations preferably form a contiguous area on the sample.

In preferred embodiments the method further comprises the step of applying aberration correction or digital refocusing to the synthetic wavefront, so as to obtain an aberration-corrected image of the plurality of locations on the sample. In certain embodiments the step of applying aberration correction or digital refocusing comprises the steps of:

(a) applying a first Fourier transform to the synthetic wavefront;

(b) applying a phase transformation function to account for focus or aberration; and (c) applying a second Fourier transform.

According to a tenth aspect of the present invention there is provided an article of manufacture comprising a computer usable medium having a computer readable program code configured to operate the apparatus of any one of the first, third, fifth or seventh aspects, or to implement the method according to any one of the second, fourth, sixth, eighth or ninth aspects.

BRIEF DESCRIPTION OF THE DRAWINGS

Preferred embodiments of the invention will now be described, by way of example only, with reference to the accompanying drawings in which:

FIG. 1A illustrates in schematic form an SD-OCT apparatus according to an embodiment of the present invention;

FIGS. 1B and 1C show enlarged views of a retro-reflective wavelength interleaver in the apparatus of FIG. 1A;

FIGS. 10A, 10B and 10C show in schematic plan view wavelength interleavers with differently structured sections for providing different sets of displacements to the various wavelengths in a dispersed beamlet or beam.

DETAILED DESCRIPTION OF THE INVENTION

Figure 2A:
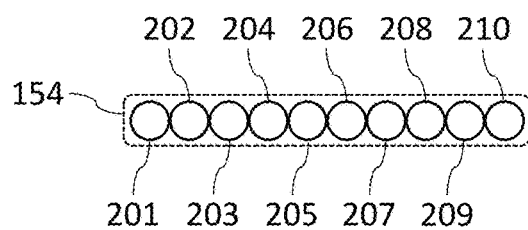
FIG. 2A depicts in schematic form the spread of wavelengths across a dispersed structured beamlet formed by the combination of a wavelength interleaver, a dispersive element and a focusing element in the apparatus of FIG. 1A.

We have previously described, in published US patent application No 2016/0345820 A1, a technique in which the interference signal from an extended sample area is sampled with a two-dimensional (2-D) lenslet array and the resulting grid of beamlets dispersed onto separate groups of pixels of a 2-D detector array. This technique, referred to hereinafter as 'Hyperparallel OCT' or 'HP-OCT', enables snapshot, and therefore motion artefact-free, acquisition of data from a sample volume with lateral (x, y) and depth (z) resolution. The present invention provides methods and apparatus for enhancing the number of sample points that can be imaged in a single frame of an HP-OCT system, or more generally for enhancing the performance of an HP-OCT system, by utilising comb slicing of the spectrum wherein individual combs of wavelengths are projected onto different areas of a sample. Alternatively, individual wavelength combs can be projected onto a given area of a sample at different times. In preferred embodiments a retro-reflector prism array is used in combination with a dispersive element and a focusing element to generate, from dispersed images of a grid of sampling beamlets, angularly or laterally separated wavelength combs that can be projected onto a sample. Snapshot, motion artefact-free analysis of the returning beamlets with a spectral domain spectrometer provides excellent phase and amplitude stability between each of the sampling beamlets in the grid.

FIG. 1A shows in schematic form a spectral domain optical coherence tomography apparatus 100 according to an embodiment of the present invention. In essence the apparatus is an HP-OCT style system modified to enhance the number of simultaneous A-scans that can be acquired in a single frame, thereby enhancing the speed with which a given sample volume can be imaged, while maintaining a large imaging depth range. The specific enhancement factor depends on a number of design considerations to be discussed below, but may for example be five, ten, 25 or 100. Vertically polarised light 102 from a broadband optical source 104 such as a polarised 50 mW superluminescent light emitting diode (SLED) with centre wavelength 840 nm and bandwidth 25 nm is collimated by a collimating element 106 such as a lens or parabolic mirror, then split into a 2-D grid of beamlets 108 with a spatial sampling element 110 in the form of a 2-D lenslet array. In one particular embodiment the lenslet array has 24×42 lenslets on a 400 µm pitch and having a focal length of 4 mm, providing a rectangular grid of 1008 beamlets 108 with a numerical aperture of approximately 0.05. The grid of beamlets is divided with an optical splitter 112 in the form of an 80:20 beamsplitting cube to provide a sample beam 114 with an average power of 10 mW and a reference beam 116 of 40 mW distributed across respective grids of beamlets, although other splitting ratios including 50:50 could be used. In other embodiments the optical splitter 112 may be in the form of a polarisation beam splitter.

After collimation at a lens 118 that may have a focal length in the range of 100 to 300 mm for example, the vertically polarised beamlets in the sample beam 114, represented by the central ray paths 119 of two beamlets, pass through a polarisation beamsplitter 120 and into a wavelength comb generator 122. In the illustrated embodiment the wavelength comb generator comprises a wavelength dispersive element 124 in the form of a transmissive diffraction grating, a focusing element 126 in the form of a lens and a wavelength interleaver 128 in the form of a retro-reflector prism array. The wavelength comb generator 122 also comprises a quarter wave plate 130 to ensure that retro-reflected beamlets are directed by the polarisation beamsplitter 120 away from the optical source 104 and towards a sample 132. The collimated beamlets 119 impinge on the diffraction grating 124 at different angles and are dispersed angularly according to wavelength, then mapped by the lens 126 onto a linear focal plane lying within the retro-reflector prism array 128. For simplicity of illustration the dispersed beamlets 134 are represented by three rays of different wavelengths from the central rays 119 of two of the beamlets 108 formed by the lenslet array 110. In reality there may be of order 3000 resolvable wavelengths across the bandwidth of the optical source 104, depending inter alia on the design of the spectrometer 182 used to analyse the interferogram obtained from a sample 132. In the illustrated embodiment the focusing element 126 is a spherical lens, although in other embodiments it may be a cylindrical lens oriented to focus the dispersed beamlets in the direction of dispersion, i.e. in the plane of the page. In yet other embodiments the focusing function is provided by appropriate design of the wavelength dispersive element 124, which may be example be a linearly chirped grating for focusing in one axis or a curved line grating for focusing in two axes. In these embodiments the wavelength dispersive element 124 and the focusing element 126 are a single element. It yet other embodiments the focusing function is provided by appropriate design of the lens 118.

In the illustrated embodiment the wavelength interleaver 128 comprises a block of transparent material 136 such as glass having an array of retro-reflective prisms 138 extending substantially perpendicularly to the dispersive axis of the grating 124, i.e. into the page, with each dispersed beamlet 134 extending across a plurality of the retro-reflective prisms 138. Preferably each dispersed beamlet extends across at least five, and up to 500, retro-reflective prisms. This factor determines the number of wavelengths, i.e. k-values, in the wavelength combs that emerge from the wavelength comb generator 122 for projection onto a sample 132, and can be chosen according to the required application. For example for wide field Doppler OCT applications such as angio-imaging it may suffice to have only a few wavelengths per wavelength comb. In general the wavelength interleaver 128 needs to be sufficiently long in the dispersive direction to provide the required number of 'teeth', i.e. individual prisms 138, per beamlet in the 2-D beamlet grid 108, noting that there may and generally will be some overlap of the dispersed beamlets 134 on the array of prisms as shown in FIG. 10C. Referring now to the enlargement shown in FIG. 1B, the included angle θ of each prism 138 is preferably 90°, although many other included angles are possible, with the transparent material 136 preferably having a sufficiently high refractive index to ensure total internal reflection at the angled facets 140 across the bandwidth of the optical source 104. Alternatively the angled facets can be coated with a reflective material such as metal, in which case the wavelength interleaver 128 can alternatively be oriented with the prisms 138 pointing towards the direction of approach of the dispersed beamlets 134. Several other configurations of wavelength interleaver with arrays of reflective elements for imparting different displacements to various selections of wavelengths in a dispersed beam or beamlet are possible, such as an array of metal-coated semi-cylindrical reflectors.

It will be apparent from FIG. 1B that the retro-reflective prisms 138 impose different displacements 142A, 142B on individual wavelengths within a dispersed beamlet, depending on where the wavelengths encounter the angled facets 140 of the prisms 138. For example a wavelength 144 that falls on the apex 146 of a prism will receive a zero displacement, while wavelengths 148, 150 that fall on an angled facet 140 to the right or left of an apex 146 will be displaced to the left or right. Since each beamlet is dispersed across a plurality of prisms 138, the effect is to impart different displacements 142A, 142B to various interleaved selections of wavelengths within the bandwidth of the optical source 104. As shown schematically in FIG. 1C, for example, the wavelength interleaver 128 imparts a first displacement 142A to a first selection of wavelengths 151 from a dispersed beamlet and a second displacement 142B to a second selection of wavelengths 153 from the dispersed beamlet, with the first and second selections of wavelengths being interleaved. Importantly, when the dispersed wavelengths are recombined by passing the retro-reflected dispersed beamlets back through the wavelength dispersive element 124, the bulk dispersion is unwound but the displacements 142A, 142B imposed on the various wavelengths within each dispersed beamlet 134 remain. The result of this is to produce, from the selections of wavelengths 151, 153, wavelength combs 135 propagating at different angles. After re-direction at the polarisation beamsplitter 120, the angularly separated wavelength combs 135 are focused with a focusing element 152 such as a lens to produce a grid of dispersed structured beamlets 154 at or near the focal plane 164 of the lens 152, each in the form of an extended line with a plurality or array of laterally separated wavelength combs. The focusing element 152 is preferably a spherical lens or similar providing focusing in two dimensions, but alternatively may be a cylindrical lens or similar providing focusing in the direction of dispersion of the wavelength dispersive element 124.

As illustrated schematically in FIG. 2A, a dispersed structured beamlet 154 may for example comprise a laterally spaced-apart array of ten wavelength combs 201, 202 . . . 210, each containing a selection of wavelengths from within the bandwidth of the optical source 104. In reality each dispersed structured beamlet will comprise a continuum of wavelength combs along its length, with the number of resolvable wavelength combs determined by the ratio of the length of the wavelength interleaver 128 to the dispersed beamlet 134 spot size, in combination with the finite pixel size of the 2-D sensor array 184 in the spectrometer 182. As mentioned previously the number of wavelengths or k-values per wavelength comb is determined by the number of prisms 138 in the wavelength interleaver 128 illuminated by each of the dispersed beamlets 134. The wavelength combs 201, 202 . . . 210 may for example each contain 100 wavelengths ($\lambda_1, \lambda_{11}, \lambda_{21}, \lambda_{31} \ldots \lambda_{991}$), ($\lambda_2, \lambda_{12}, \lambda_{22}, \lambda_{32} \ldots \lambda_{992}$) . . . ($\lambda_{10}, \lambda_{20}, \lambda_{30}, \lambda_{40} \ldots \lambda_{1000}$) selected from 1000 resolvable wavelengths. Because the wavelengths in the various wavelength combs are interleaved, the bandwidth of each wavelength comb is substantially equal to the bandwidth of the optical source 104. In this example the wavelength combs have a tenfold reduction in the number of k-values compared to the unstructured beamlets 108.

The grid of dispersed structured beamlets 154 then passes to a scanning mirror 158 for adjusting the on-sample location of the grid and a lens system 160 for projecting the dispersed structured beamlets onto a sample 132, which may for example be the cornea or retina of an eye or some other biological or non-biological sample. In the illustrated embodiment the focusing element 152, scanning mirror 158 and lens system 160 form a relay system 156 that, in combination with the wavelength dispersive element 124, form at least first and second wavelength combs 201, 202 from at least first and second selections of wavelengths 151, 153 and project the wavelength combs onto the sample 132. With the source light 102 sampled by a 2-D lenslet array 110, the relay system 156 projects multiple sets of wavelength combs, i.e. multiple dispersed structured beamlets 154, onto a plurality of regions of the sample to form a 2-D illumination grid 212 as shown schematically in FIG. 2B. In this particular embodiment the lenslet array 110 and grating 124 are oriented with respect to each other such that the beamlets are dispersed in a direction parallel to an axis 214 of the beamlet grid 108 provided by the lenslet array 110. In alternative embodiments other components may form a relay system. Recalling that the wavelength dispersive element 124 converts a plurality of selections of wavelengths 151, 153 to a plurality of wavelength combs 135 propagating at different angles, the wavelength dispersive element 124 can function as a relay system for a sample such as an eye placed at or near the location of the focusing element 152. In this case the optical power elements of the eye would perform the role of the focusing element 152, forming a grid of dispersed structured beamlets 154 on the retina, each in the form of an extended line with a plurality or array of laterally separated wavelength combs 201, 202 etc.

The form of the lens system 160 can be chosen according to the application, with the illustrated demagnifying configuration being suitable for imaging the cornea of an eye or some other near-surface structure of a sample. For retinal imaging the lens system 160 should be designed with consideration of the eye's refractive power, and may for example comprise a 4F relay with magnification or demagnification and focus adjustments for the prescription of the eye being examined as is known in the art. In certain embodiments the lens system 160 or the entire optical relay 156 are interchangeable to suit different samples or applications.

Figure 3:
FIG. 3 shows in schematic form portions of spectra incident at different positions spaced 10 µm apart along a sample, from one dispersed structured beamlet.
Figure 3:
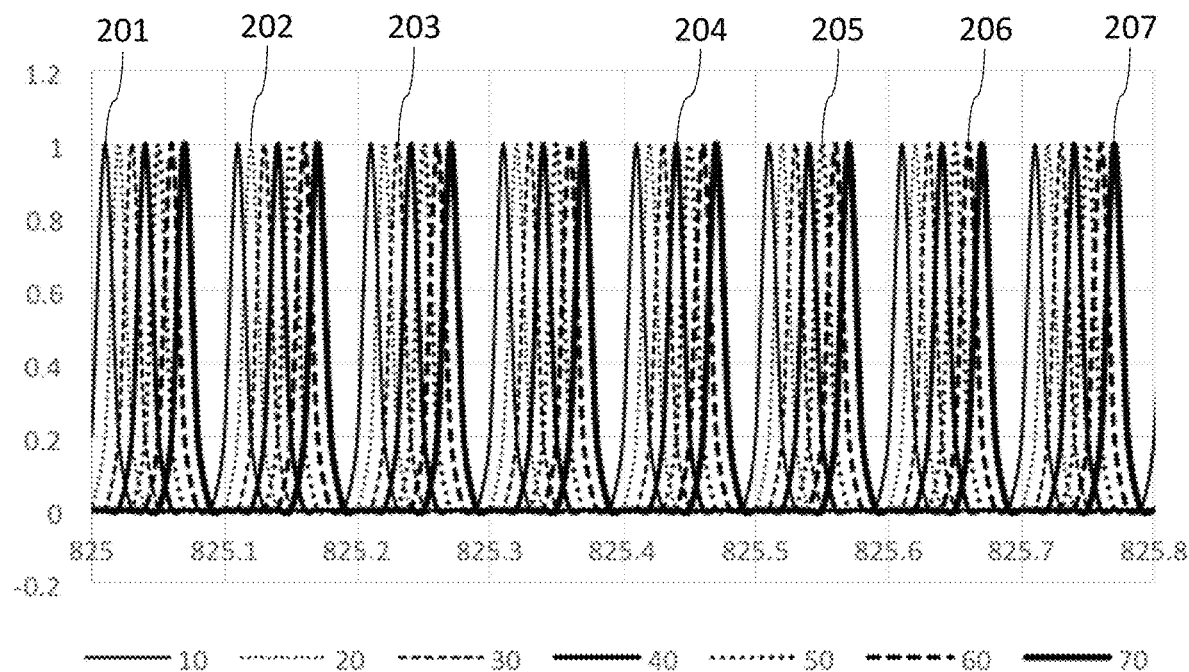

FIG. 3 shows in schematic form portions of the spectra incident at different positions along a sample, from one dispersed structured beamlet 154. In this particular example the dispersed structured beamlet comprises ten laterally spaced-apart wavelength combs 201, 202 . . . 210 as shown in FIG. 2A, that impinge on the sample at points 10 μm apart, although for clarity only seven of the wavelength combs 201 . . . 207 are shown. An optical coherence tomogram can be generated from each wavelength comb at the different points on the sample, and it will be appreciated that because the bandwidth of each of the wavelength combs is substantially equal to the bandwidth of the optical source 104, there will be minimal reduction in depth resolution at the sample points compared to what would be provided by the unstructured beamlets 108.

Returning to FIG. 1A, we now consider the return path of light from the sample 132. A portion of the light 162 scattered or reflected from various points on the sample passes back through the optical relay 156 on retro-reflected return paths, so that for each wavelength of each beamlet there is a component travelling in the opposite direction at the focal plane 164 of the lens 152. This retro-propagating light is collimated by the lens 152 then redirected by the polarisation beamsplitter 120 back into the wavelength comb generator 122, for dispersion at the grating 124 onto the wavelength interleaver 128. This time the prisms 138 of the wavelength interleaver 128 apply the opposite displacements to the displacements applied in the first pass, and consequently the back-scattered beamlets are recovered following the second pass through the grating 124. That is, the spectral form of the original beamlets 108 is recovered. The recovered beamlets are combined with the undispersed reference path beamlets 168 at the 80:20 beamsplitter 112, with 80% of the light in the recovered beamlets being combined with 20% of the light in the reference path beamlets 168. The distance between the beamsplitter 112 and the reference path reflector 170 is not shown to scale in FIG. 1A, but should correspond approximately to the optical path length from the beamsplitter 112 to the sample 132 via the wavelength comb generator 122. Relay optics 172 and dispersion compensating elements 174 may also be present in the reference arm.

Figure 2B:
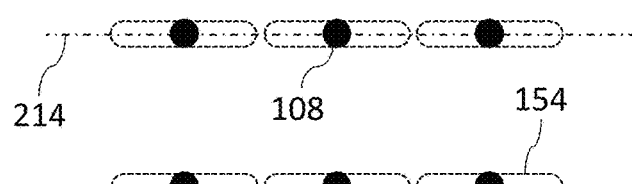
FIG. 2B illustrates schematically the on-sample projection of a grid of dispersed structured beamlets, according to an embodiment of the present invention.

The combined beamlets 166 enter a detection system 176 where they are spatially filtered with a 2-D aperture array 178 to remove stray or multiple-scattered light, and optionally re-sized with a 2-D lenslet array 180, before being analysed in a multi-beam spectrometer 182 such as that described in published PCT patent application No WO 2018/000036 A1 entitled 'Apparatus and method for confocal microscopy using dispersed structured illumination' Phase and amplitude data from a plurality of sample points in the 2-D illumination grid 212 shown in FIG. 2B, encoded in the combined beamlets 166, are recorded by a 2-D sensor array 184 and read out in a single frame for processing in a processor 186 equipped with suitable machine-readable program code to obtain a tomographic profile of the sample 132 at each illuminated point. If each dispersed structured beamlet 154 has ten resolvable wavelength combs 201 . . . 210 as shown in FIG. 2A, phase and amplitude data can be recorded from ten sample points per beamlet, representing a tenfold enhancement in the number of points that can be imaged in a single frame. In the absence of the speed enhancement provided by the present invention, i.e. if the 2-D grid of beamlets 108 were to proceed directly to the sample 132 rather than via the wavelength comb generator 122, or if the wavelength interleaver 128 were replaced by a plane mirror, the spectrometer 182 may for example provide a 9.4 μm axial resolution over a depth of 11 mm in air, and be able to sample 1008 A-scans simultaneously at a 300 Hz frame rate. With a factor of Z speed enhancement provided by Z resolvable wavelength combs per beamlet, the spectrometer 182 would be able to sample Z×1008 A-scans simultaneously with the same frame rate and axial resolution. The unambiguous depth range would be reduced to 11/Z mm, although the total depth range that can be imaged, with ambiguity, would remain at 11 mm.

Figure 4A:
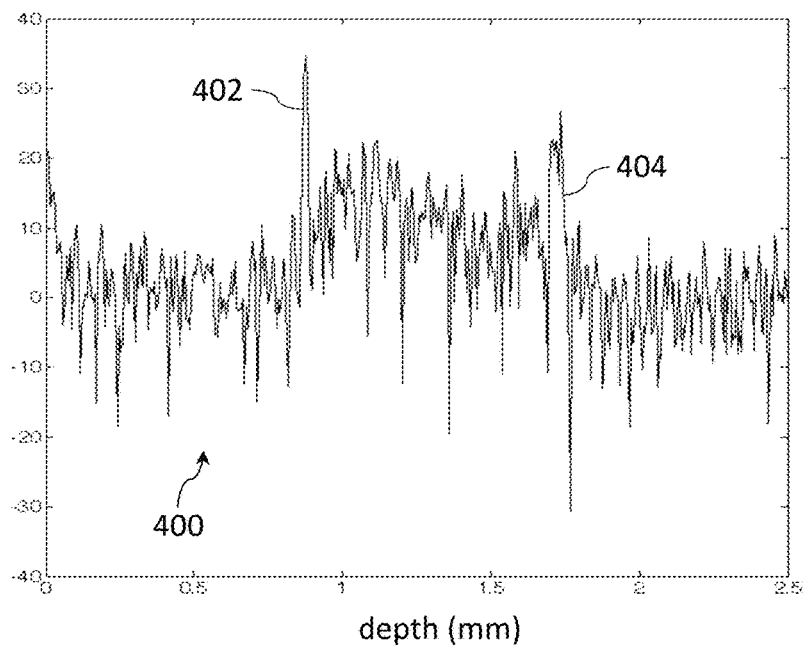
FIG. 4A shows an A-scan of corneal tissue illuminated with a full spectrum beamlet.
Figure 4B:
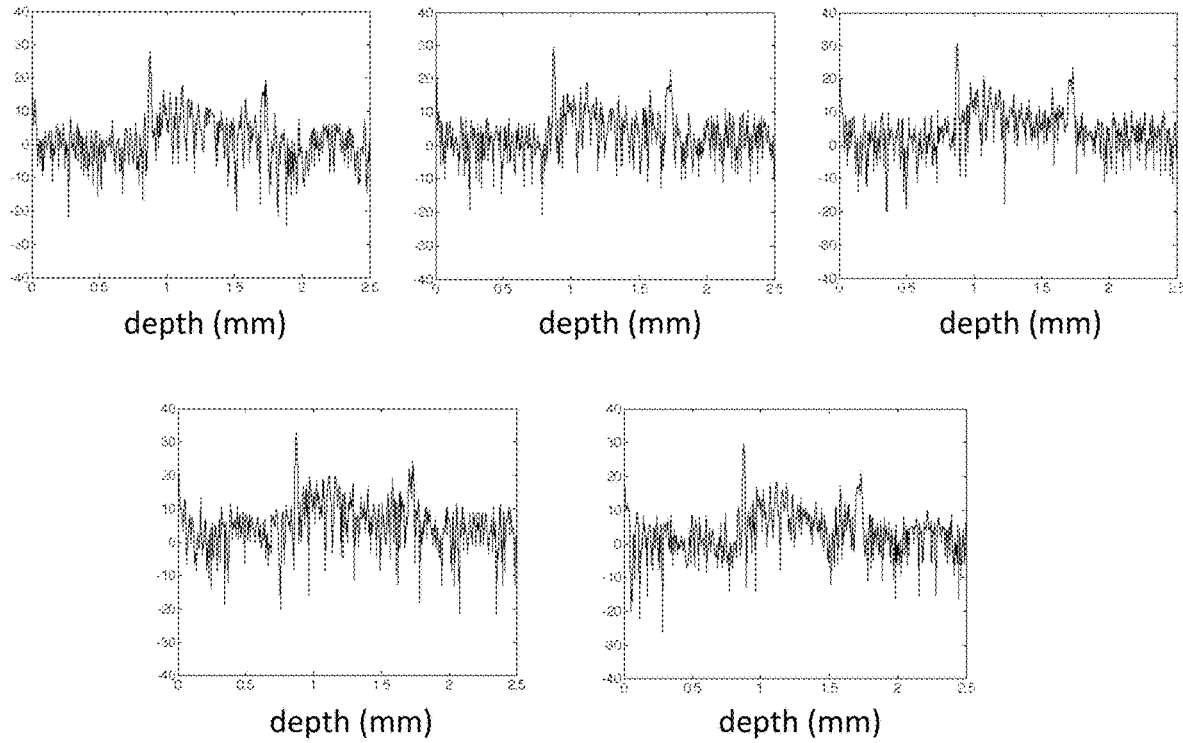
FIG. 4B shows five versions of the A-scan shown in FIG. 4A, each numerically down-sampled by a factor of five by extracting different sets of every fifth k-value.

FIG. 4A shows an A-scan 400 of corneal tissue illuminated with a full spectrum beamlet with an on-sample spot size of approximately 11 μm, e.g. using an OCT apparatus where beamlets 108 proceed from the broadband source 104 directly to the sample 132 rather than via the wavelength comb generator 122. The anterior and posterior surfaces of the cornea are indicated by the peaks 402 and 404 in the A-scan 400. FIG. 4B shows for comparison five versions of the A-scan shown in FIG. 4A, each numerically down-sampled by a factor of five by extracting different sets of every fifth k-value. This is to simulate the parallel acquisition of A-scans from five laterally separated points on the cornea using optically sub-sampled wavelength combs of a dispersed structured beamlet 154. As noted previously the number of A-scans that can be acquired in parallel depends on the number of resolvable wavelength combs in a dispersed structured beamlet. It can be seen that there is a reduction in signal-to-noise ratio in the simulated A-scans of FIG. 4B, indicative of the fivefold reduction in power in each wavelength comb, but the image resolution is unaffected and the signal doesn't drop off with imaging depth. This simulation shows that A-scans from a plurality of laterally separated points on a sample can be captured in a single frame to enhance acquisition speed, with minimal reduction in image quality.

Figure 5A:
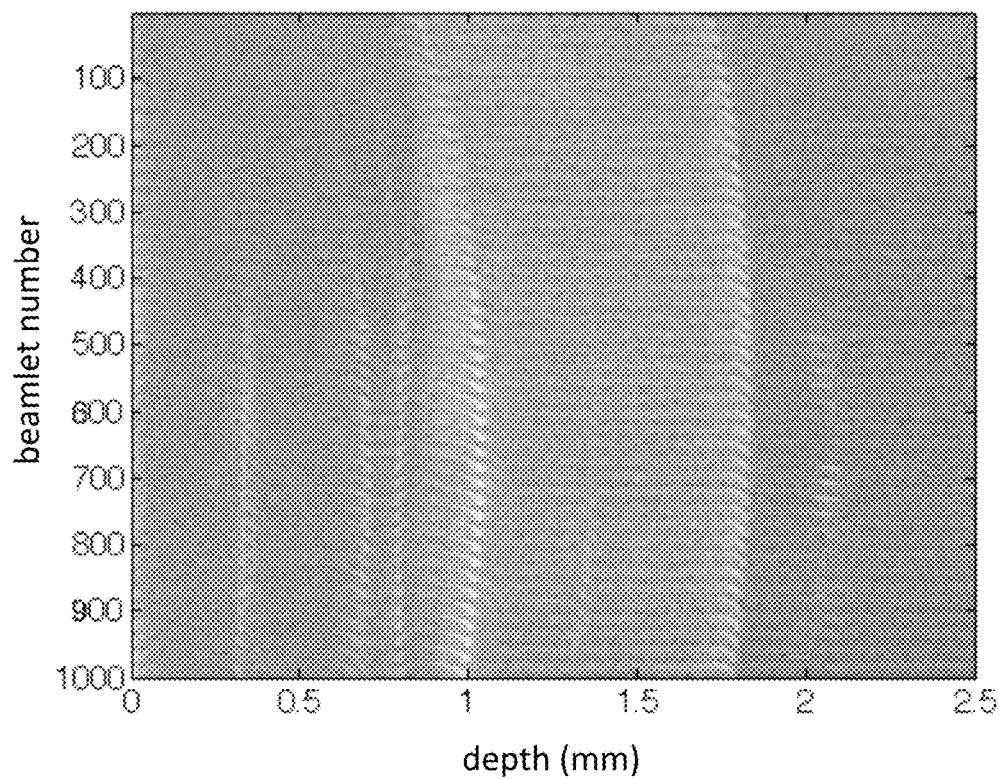
FIG. 5A depicts a representation of a sparse volume C-scan of a cornea that would be generated by Fourier transformation of a single frame with a grid of 1000 full spectrum beamlets.
Figure 5B:
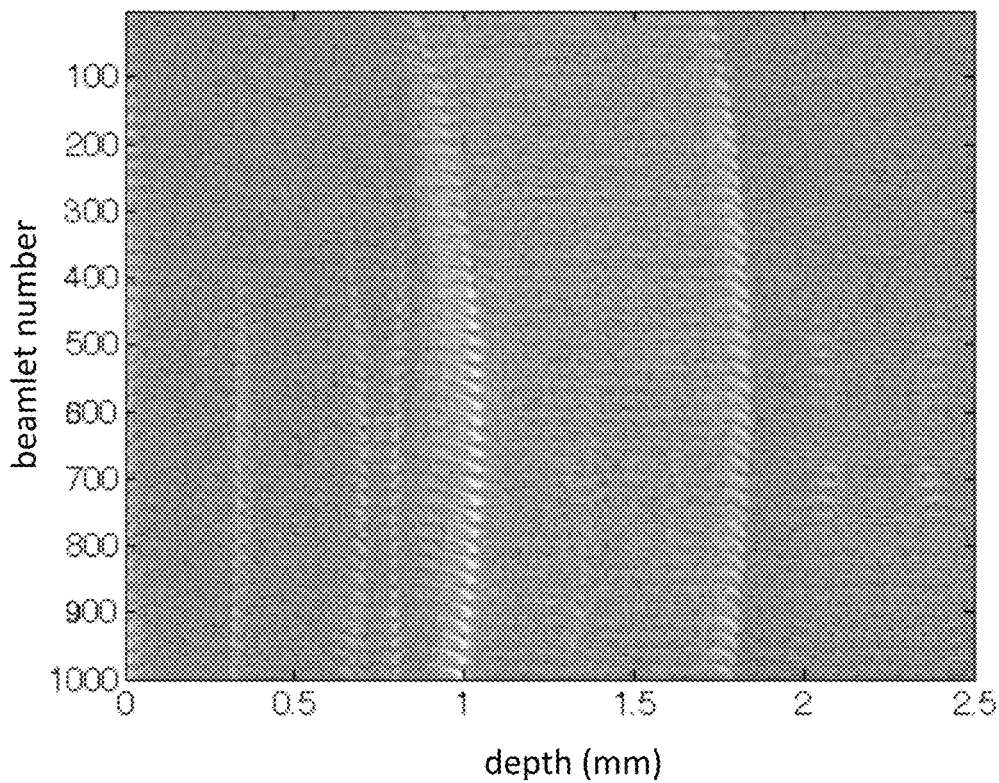
FIG. 5B depicts a simulation of the dispersed structured beamlet representation of the same frame as in FIG. 5A, generated using one of the down-sampled A-scans of FIG. 4B.

To aid in visualisation, FIG. 5A depicts a representation of a sparse volume C-scan of a cornea that would be generated by Fourier transformation of a single frame with a grid of 1000 full spectrum beamlets. FIG. 5B depicts a simulation of the dispersed structured beamlet representation of the same frame, generated using one of the sub-sampled A-scans of FIG. 4B, to demonstrate the effect of the fivefold sub-sampling. Again, there is minimal reduction in image quality.

As noted previously, optical sub-sampling trades off unambiguous imaging depth for acquisition speed. Noting that samples such as the retina or cornea generally have features that extend in layers perpendicular to the incident beam direction, to obtain information on features well away from the focal plane of a dispersed structured beamlet it is possible to create a synthetic extended depth A-scan from the multiple individual wavelength combs in the dispersed structured beamlet. In ocular samples this would for example be useful for identifying any hyperreflectivity or scattering in the aqueous humour, vitreous humour or retina associated with uveitis. Although such scattering centres may not all be close to the focal plane of the dispersed structured beamlets, the summed spectra of several or all of the wavelength combs can be used to generate a reduced resolution image over an extended depth that can be fused with high resolution imaging of the cornea or retina, effectively obviating the reduction in unambiguous imaging depth caused by the sub-sampling.

Figure 6:
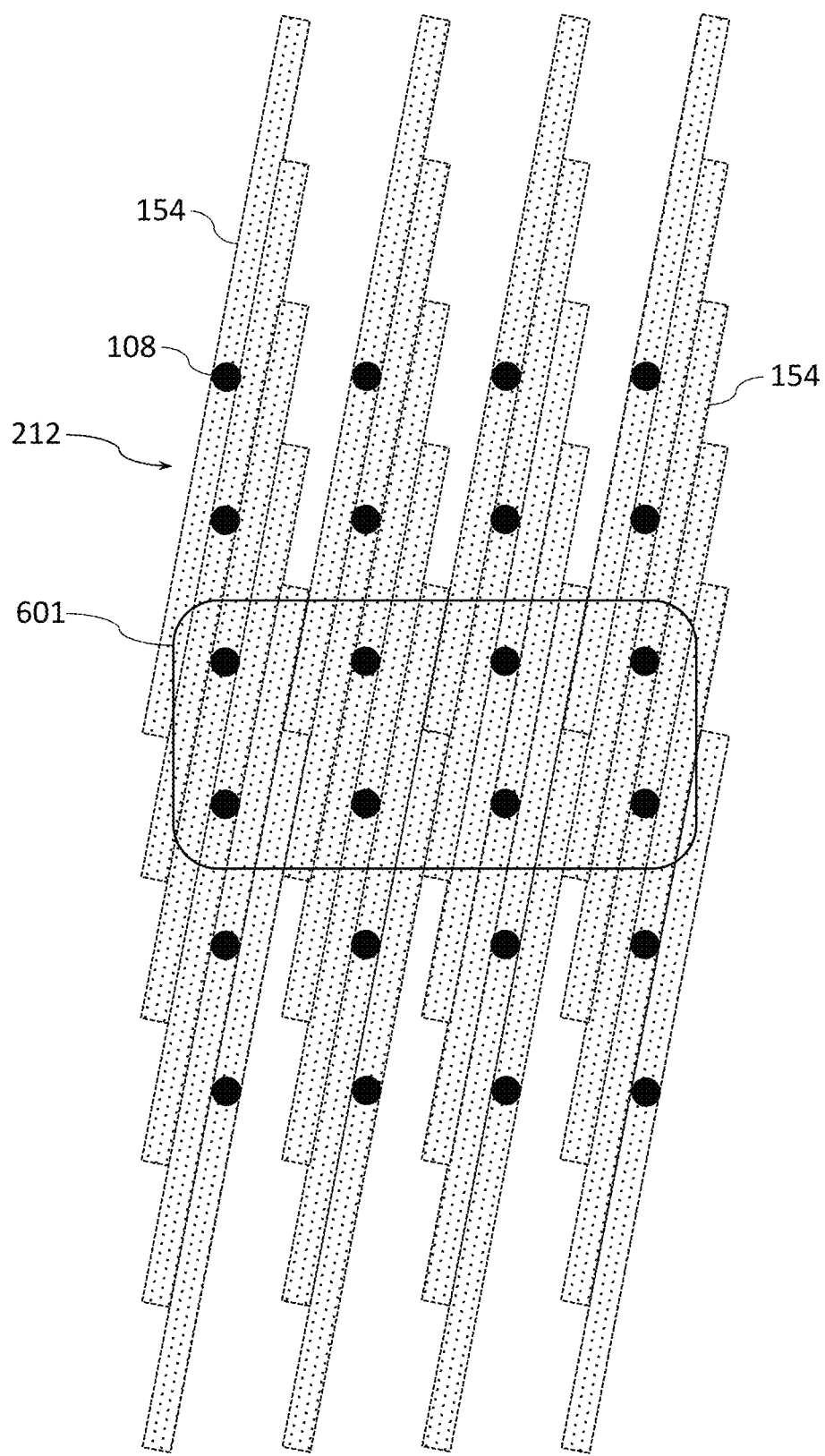
FIG. 6 illustrates schematically the on-sample projection of a grid of dispersed structured beamlets, according to an embodiment of the present invention.

The previously described embodiment demonstrated how OCT acquisition speed across an extended area of a sample can be increased by generating and projecting a grid of dispersed structured beamlets onto the sample. We now describe how the principles of the present invention also allow numerical aberration correction or digital refocusing in addition to increased acquisition speed. To this end, in another embodiment of the invention the OCT apparatus shown in FIG. 1A is configured to provide substantially contiguous coverage of a sample area with a grid of dispersed structured beamlets. In one particular example the apparatus is configured to provide a factor of 25 enhancement to the number of simultaneous A-scans that can be acquired while maintaining a large imaging depth range, with the 2-D lenslet array 110 selected to provide beamlets 108 with a spot size to grid ratio of 1:5 at the sample 132 and oriented with respect to the dispersive axis of the grating 124 such that individual beamlets 108 are dispersed at an angle of 12° to the beamlet grid. FIG. 6 shows in schematic form how a 2-D illumination grid 212 of dispersed structured beamlets 154 provided by this combination of angle and on-sample spot size to grid ratio, calculated for the original beamlets 108 produced by the lenslet array 110, achieves substantially contiguous coverage of a sample area 601.

To achieve the dense sample coverage shown in FIG. 6 the size of each prism 138 in the wavelength interleaver 128 is chosen to be 25 times the resolvable wavelength size at the focal plane 164 or at the sample 132. In an alternative configuration the apparatus 100 is configured to provide a 1:10 spot size to grid ratio at the sample, with beamlet dispersion at 6° to the beamlet grid and 100 wavelength combs, i.e. sampling points, per beamlet. With the ratio of aperture area in the aperture array 178 to on-sample illuminated area effectively increased from 1:25 to 1:100, this provides an additional 6 dB rejection of multiple scattered light. However this comes at the expense of a reduced number of k-values per sampling point as the resolvable wavelengths are spread among a larger number of wavelength combs, e.g. 30 k-values per sampling point if 3000 effective k-values are divided among 100 wavelength combs. We still have access to phase and amplitude across an extended region 601 of a sample for numerical aberration correction or digital refocusing through the imaged depth, as well as the coherence gating, but the trade off for the increased rejection of multiple scattered light is a reduced number of k-values, implying a more limited depth range over which we can unambiguously reconstruct data from any individual A-scan.

The on-sample spot size to grid ratio can be controlled by choice of the focal length of the lenslet array 110, with focal length in the range of 6 to 15 mm being typical for obtaining dense or substantially contiguous sample coverage as shown in FIG. 6. Because the beamlets will now have a lower NA than in the first described embodiment where the lenslet array 110 had a focal length of 4 mm, the focal length of the lens 118 needs to be correspondingly increased to create an adequate fill of the grating 124 for separation of the wavelengths at the wavelength interleaver 128. To maintain a compact apparatus it is possible to demagnify the image of the beamlets 108 to increase their NA before collimating them. Accordingly, in certain embodiments the lens 118 is a compound lens for providing collimated beamlets that are roughly overlapping with beam size in the region of 10 to 30 mm at the grating 124 depending on requirements. Upon focusing to the wavelength interleaver 128 each resolvable location within a grid will contain a distinct wavelength spectrum, i.e. comb of wavelengths.

Because we now have full access to the phase and amplitude of the scattered light over an extended area 601 of a sample, as shown in FIG. 6, numerical aberration correction or digital refocusing of the data read out by the processor 186 can be applied as described below. Numerical aberration correction and digital refocusing techniques can still be applied to data obtained from an extended area 601 even if the beamlet coverage is not fully contiguous, but will be more accurate when the coverage is more complete. Furthermore the aperture array 178 provides confocal gating for removal of unwanted multiple-scattered light. The apparatus 100 is a novel form of HP-OCT, i.e. snapshot full field OCT, with enhanced acquisition speed, and with confocal gating improving the best achievable resolution relative to plane wave illumination, as well as reducing the impact of multiple scattering.

Although an appropriately designed grid of dispersed structured beamlets 154 can provide access to phase and amplitude information at each point across an extended area 601 of a sample as shown in FIG. 6, the information is on a number of different sets of wavelength combs. To apply numerical adaptive optics techniques such as aberration correction or digital refocusing, a synthetic or nominal wavelength comb can be created to which the different A-scans can be normalised, then treated as a whole volume. Accordingly, in certain embodiments the invention provides a method for reconstructing a synthetic or nominal wavelength comb across an area of a sample, to enable numerical adaptive optics such as aberration correction or digital refocusing, comprising:

(i) Simultaneously detecting a plurality of signals comprising light in a plurality of interleaved wavelength combs reflected or scattered from a plurality of locations on a sample; and (ii) Scaling the relative phase of the plurality of signals to account for the different wavelengths in the wavelength combs, to create a synthetic wavefront across the plurality of locations on the sample.

In preferred embodiments the scaling is a function of the distances of the plurality of locations from the zero point delay, i.e. the point at or near the sample where the optical path lengths of the sample and reference arms are equal. Essentially, step (i) associates, with each resolvable location across a sample area, a signal such as an A-scan comprising a specific comb spectrum from a specific grid point, while step (ii) rescales each of the wavelength comb spectra to have the correct phase as if each contained the same wavelengths, e.g. as if each A-scan were generated from the same set of k-values. Once the A-scans have been scaled to provide consistent phase and amplitude for the synthetic or nominal wavefront, aberration correction can be applied. This may for example be achieved by Fourier transforming the complex function over a given area, applying a phase transformation function to account for focus and/or aberration, then applying another Fourier transform to recover the aberration-corrected image.

The near field aberration and/or focus correction is thus able to provide a very high resolution image of various features in a sample, e.g. retinal features, at different depths corresponding to the chosen coherence gate or OCT tomogram pixel. Importantly, snapshot acquisition over an entire contiguous or near-contiguous illuminated area 601 provides the phase stability necessary for application of aberration correction or digital refocusing, and the use of confocal gating provides advantages over conventional full field approaches in terms of achievable resolution and reduction of noise from multiple scattering.

Figure 7A:
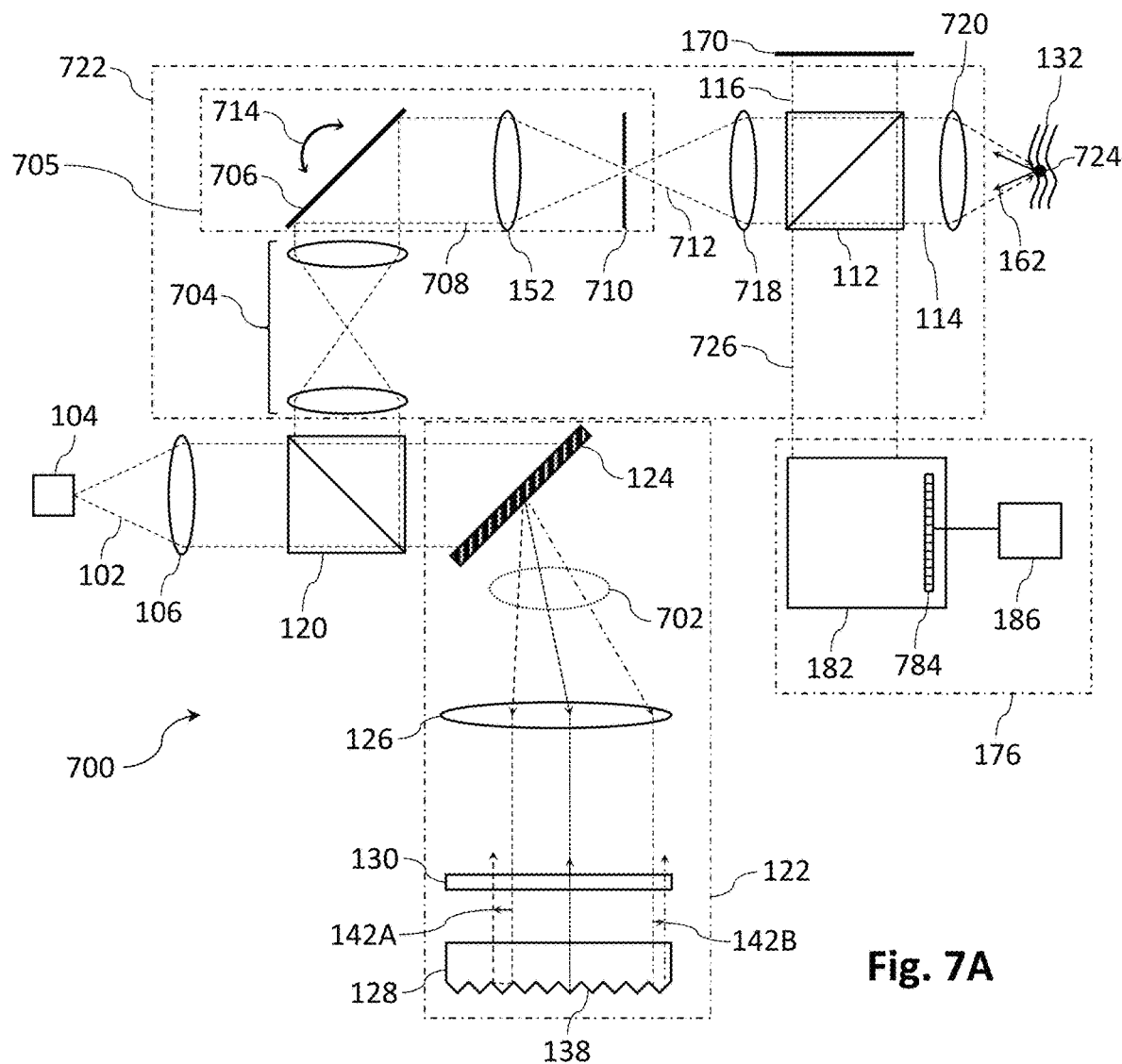
FIG. 7A illustrates in schematic form an SD-OCT apparatus according to an embodiment of the present invention.

FIG. 7A shows in schematic form a spectral domain optical coherence tomography apparatus 700 according to another embodiment of the present invention. The apparatus 700 includes many elements that are in common with the apparatus 100 depicted in FIG. 1A, and these common elements are designated with the same reference numerals. Similar to the apparatus 100, the apparatus 700 generates a plurality of laterally spaced wavelength combs. However instead of projecting the wavelength combs simultaneously onto a sample, the apparatus 700 is designed to direct a temporal sequence of wavelength combs onto a sample. In certain embodiments the wavelength combs are directed onto the same area of a sample, thereby illuminating and capturing that area at different times, with the wavelength comb selection being sufficiently rapid for the series of A-scans to be acquired in a single frame via different sets of pixels of a sensor array 784. For example with a series of ten resolvable wavelength combs the effective frame rate would be increased from 300 Hz to 3 kHz. This enhancement of the effective frame rate may be useful for example for angio-imaging applications where it is desirable to be able to track phase motion over different time frames for quantitative assessment of blood flow rates. The provision of sub-ms frame rates would also be advantageous for tracking elastographic waves over a cornea, which has a sufficiently small thickness for depth range limitations associated with the optical subsampling to be insignificant. In other embodiments the wavelength combs are directed onto different areas of a sample, e.g. for faster wide field imaging.

As will be shown, in the apparatus depicted in FIG. 7A the structured dispersion is applied to an entire beam from an optical source rather than to individual beamlets, which simplifies the relay optics, and only a single aperture is required rather than an aperture array. As such, this approach can be advantageously applied to the holoscopic technique described in published US patent application No 2016/0345820 A1, by aperture-filtering the input illumination beam, and therefore both the sample and reference beams.

Referring to the apparatus 700 shown in FIG. 7A, vertically polarised light 102 from a broadband optical source 104 such as a SLED is collimated by a collimating element 106 such as a lens or parabolic mirror, then directed to a polarisation beamsplitter 120 that is configured to pass the vertically polarised light 102 without deflection into a wavelength comb generator 122. A wavelength dispersive element 124 such as a diffraction grating applies a wavelength-dependent angular deflection to the incoming light such that, upon focusing by a focusing element in the form of a lens 126, the individual wavelengths 702 are dispersed along a wavelength interleaver 128 in the form of a retro-reflector prism array. This wavelength interleaver imparts different displacements 142A, 142B to different selections of individual wavelengths 702 depending on where the wavelengths encounter the angled facets of the individual prisms 138 of the wavelength interleaver 128. Double passage through a quarter wave plate 130 rotates the polarisation state by 90°, so that light exiting the wavelength comb generator 122 is redirected at the polarisation beamplitter 120 away from the optical source 104 and towards a lens system 704 and a wavelength comb selector 705. The second passage through the diffraction grating 124 unwinds the bulk dispersion but not the displacements 142A, 142B imposed on different selections of wavelengths by the wavelength interleaver 128, to produce a number of wavelength combs propagating at different angles.

Figure 7B:
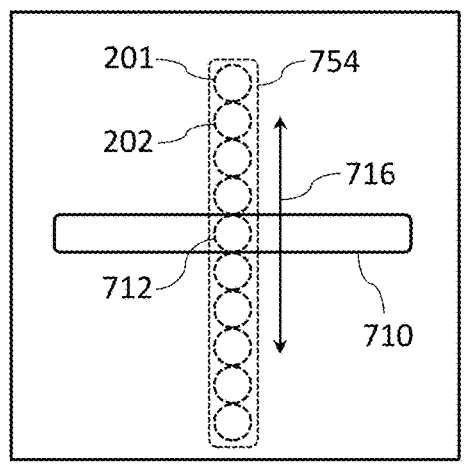
FIG. 7B depicts the selection of a wavelength comb in the FIG. 7A apparatus by scanning a dispersed structured beam across an aperture.

Within the wavelength comb selector 705, a beam steering element 706 such as a MEMS mirror applies a common angular shift to all of the wavelength components of the relayed light 708, which are then imaged by a focusing element such as a lens 152 to produce, at the plane of an aperture 710, a dispersed structured beam similar to the dispersed structured beamlet 154 shown in FIG. 2A. As shown schematically in FIG. 7B, this dispersed structured beam 754 can be depicted as a laterally spaced series of wavelength combs 201, 202 etc each comprising an interleaved selection of wavelengths from the optical source 104. The aperture 710 is sized to transmit a single resolvable wavelength comb 712, although in reality there will be a continuum of wavelength combs along the dispersed structured beamlet 754. Rotational adjustment 714 of the beam steering element 706 results in translation 716 of the dispersed structured beam 754 across the aperture 710, allowing selection of a wavelength comb 712. Returning to FIG. 7A, a selected wavelength comb 712 is collimated by a collimation element 718 for use as the input beam for an OCT interferometer comprising a beamsplitter 112 for separating and recombining the selected wavelength comb 712 into sample and reference beams 114, 116, and a reference path reflector 170. A system of optics 720, represented here by a single lens although other components may be present, serves to direct the selected wavelength comb onto the sample 132 and collect return light 162 scattered or reflected from the sample. The return light is recombined with the reference beam 116 and the resulting interferogram 726 detected and analysed in a detection system 176 comprising a spectrometer 182 with a sensor array 784, and a processor 186 equipped with suitable machine-readable program code, to obtain a tomographic profile of the sample 132.

Figure 8:
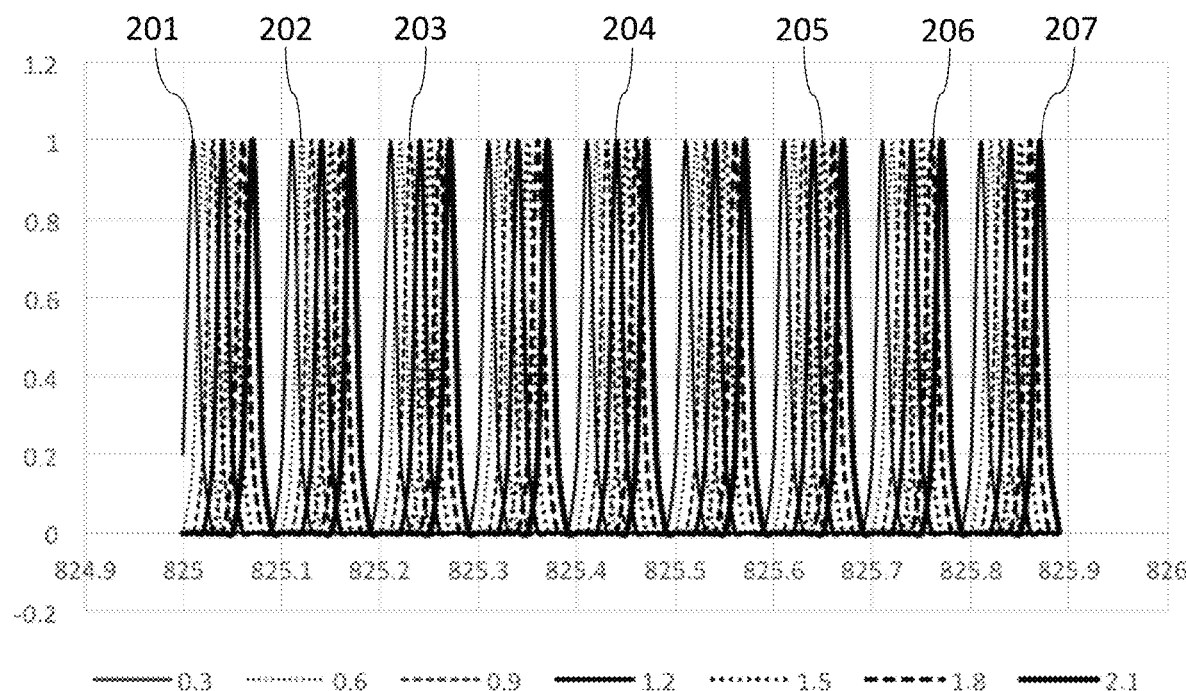
FIG. 8 shows schematically a time sequence of wavelength combs incident on a sample.

In the illustrated embodiment the lens system 704, wavelength comb selector 705, collimation element 718 and beam directing optics 720 form a relay system 722 that, in combination with the wavelength dispersive element 124, form a plurality of wavelength combs 201, 202 etc and project a sequence of selected wavelength combs 712 onto a sample 132. In the illustrated embodiment the relay system 722 is configured to project the sequence of wavelength combs onto a single region 724 of the sample 132, e.g. for angio-imaging applications as mentioned previously. In other embodiments the relay system 722 is configured to project the sequence of wavelength combs onto different regions of the sample, e.g. for wide field imaging, in which case the beam directing optics 720 may include a second beam steering element operable in conjunction with the beam steering element 706. Either way, the selected wavelength comb 712 incident on the sample can be modified over time by angularly scanning the beam steering element 706, as depicted for example in FIG. 8 which shows a sequence of seven wavelength combs 201, 202 . . . 207 transmitted through the aperture 710 at times 0.3, 0.6 . . . 2.1 ms for interaction with one or more regions of the sample 132. As in the previous embodiments, the bandwidth of each wavelength comb is substantially equal to the bandwidth of the optical source 104 so there will be essentially no reduction in axial resolution. The interferograms 726 corresponding to each of the sequentially selected wavelength combs can be dispersed onto separate sets of pixels of the sensor array 184 for snapshot acquisition in a single frame, thereby enhancing the effective frame rate of the apparatus 700. In these embodiments, where the wavelength combs incident on the sample 132 are obtained from a single dispersed structured beam 754 rather than from a plurality of dispersed structured beamlets 154 as in the apparatus 100 shown in FIG. 1A, it suffices for the detector array 184 to be a 1-D array. Individual pixels within a 1-D detector array can be mapped to a resolvable wavelength within a particular wavelength comb incident on a particular region of the sample at a particular time.

In the illustrated embodiments the wavelength-dependent dispersion in the wavelength comb generator 122 is provided by a transmissive grating 124, although the dispersion could be provided by many other components such as prisms or reflective gratings. A very high order surface relief grating or a sampled phase grating will have cyclical dispersion properties, and would be lighter and simpler to manufacture for hand held OCT apparatus if it can be appropriately blazed to suppress unwanted orders. Alternatively, unwanted orders of a grating can be removed by aperturing.

Figure 9:
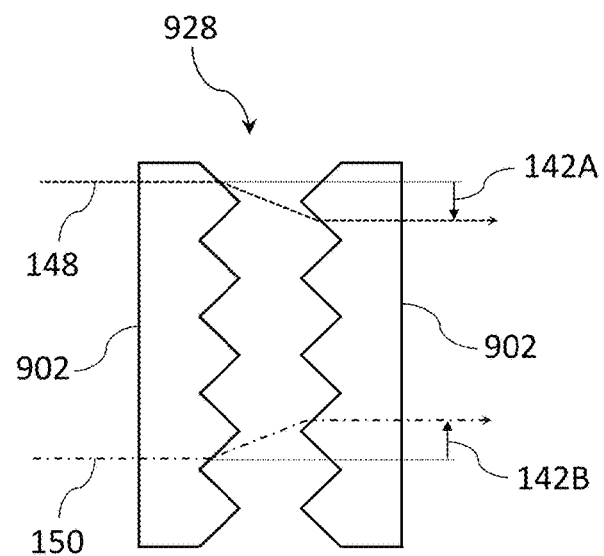
FIG. 9 illustrates schematically a wavelength interleaver operating in a transmissive configuration.

Although the foregoing description has been limited to retro-reflective configurations for generating combs of wavelengths, similar results can also be achieved with transmissive configurations, for example using multiple image inversion with a wavelength interleaver 928 in the form of a pair of prism arrays 902 that apply different displacements 142A, 142B to different wavelengths 148, 150 as shown schematically in FIG. 9. Similar results would be obtained with a pair of cylindrical lenslet arrays. In configurations where the wavelength interleaver is transmissive, or reflective but not retro-reflective, wavelength dispersive elements can be provided on both sides of the wavelength interleaver, one for angularly dispersing a plurality of wavelengths onto the wavelength interleaver and one for recombining the interleaved wavelengths to produce an array of wavelength combs. Additionally, the pitch of the retro-reflective prisms 138 or other wavelength-interleaving elements can be modified to account for any nonlinearity in the dispersion of the wavelength dispersive element, or grid distortion of the relay or projection optics.

In alternative embodiments a wavelength comb generator 122 for use in an apparatus 100 or 700 includes a wavelength interleaver having two or more differently structured sections for providing different sets of displacements 142A, 142B to the various wavelengths in a dispersed beamlet 134 or beam. For example FIGS. 10A and 10B show in schematic plan view wavelength interleavers 1028 with a first section 1002 comprising an array of retro-reflective prisms 1008 on a smaller pitch, a second section 1004 comprising an array of retro-reflective prisms 1010 on a larger pitch and a third section 1006 comprising a plane reflector, with the section accessed by one or more dispersed beamlets or beams controllable for example by mechanical translation of the wavelength interleaver 1028. FIG. 10C depicts in schematic plan view another form of wavelength interleaver 1028 in which differently structured sections 1002, 1004 and 1006 are interleaved in the direction orthogonal to the dispersive axis. This form of wavelength interleaver may be suitable for example for interleaving a grid of dispersed beamlets 134 focused in two axes, i.e. parallel and orthogonal to the dispersive axis, with the section accessed by the beamlets adjustable by a small mechanical translation 1012. In any of these embodiments, a dispersed beamlet or beam incident on the prisms 1008 or 1010 of the first or second sections 1002 or 1004 will be converted to a dispersed structured beamlet or beam having wavelength combs with a greater or lesser number of k-values, while dispersed beamlets or beams incident on the plane reflector of the third section 1006 will emerge from the wavelength comb generator in the same form as they entered. Consequently, when the wavelength interleaver 1028 is in the 'plane reflector' position the apparatus 100 of FIG. 1A for example will probe a sample 132 with a grid of undispersed beamlets 108 as in standard HP-OCT. This offers no speed enhancement but may be useful for aligning the apparatus or making comparative measurements for example. In yet other embodiments the wavelength comb generator 122 or wavelength interleaver 128, 1028 is interchangeable to suit different applications or samples.

In the apparatus 100 the wavelengths 162 scattered or reflected from a sample 132 are recombined by reversing the path through the wavelength comb generator 122 before entering the spectrometer 182, however in alternative embodiments it is possible to use other combinations of aperturing and dispersion to project each wavelength onto a different set of pixels of a 2-D detector array 184.

The apparatus 100 shown in FIG. 1A and the apparatus 700 shown in FIG. 7A are SD-OCT systems employing light from a broadband optical source 104, so that all of the wavelength combs 201, 202 etc in a dispersed structured beamlet 154 or beam 754 are present simultaneously. Alternatively, in SS-OCT embodiments the broadband optical source is replaced by a swept source, in which case the wavelength combs and the k-values within them are generated sequentially as the wavelength of the swept source is scanned. Provided the wavelength scanning rate is sufficiently fast, however, the wavelength combs 201, 202 etc in FIG. 1A can still be generated and projected onto a sample 132 in a sufficiently short time for the resulting interferograms to be captured in a single frame of a 2-D sensor array 184. Many commercially available swept sources can be scanned over a wavelength range of tens of nm in less than 100 μs, easily fast enough for single shot acquisition with a 2-D sensor array having a frame rate of, say 300 Hz. Similarly, swept sources can generally be scanned more rapidly than the beam steering element 706 of the wavelength comb selector 705, so that a swept source version of the apparatus 700 in FIG. 7A is still able to project a sequence of selected wavelength combs 712 onto a sample 132 for enhancing the effective frame rate.

Although the generation and application of wavelength combs has been described with respect to an HP-OCT system, the same principles can be applied to other OCT systems such as line field OCT, single or multi-beam scanning SD-OCT, or SS-OCT. The generation and application of wavelength combs can also be used to enhance the speed of non-interferometric imaging modes such as hyperspectral imaging and confocal microscopy, with the reference beam 116 blocked or the reference path optics removed for example.

Although the invention has been described with reference to specific examples, it will be appreciated by those skilled in the art that the invention may be embodied in many other forms.

The invention claimed is:

1. An optical coherence tomography apparatus comprising:
    an optical source for emitting a plurality of wavelengths;
    a wavelength comb generator for generating two or more wavelength combs containing interleaved selections of wavelengths from said plurality of wavelengths;
    a relay system for projecting said two or more wavelength combs onto a sample;
    a detection system for detecting, in a single frame of a two-dimensional sensor array, light in said two or more wavelength combs reflected or scattered from said sample; and
    an optical splitter for splitting light from said optical source into a sample beam and a reference beam, and for recombining said sample and reference beams after said sample beam has interacted with said sample, such that said detection system is able to obtain a tomographic profile of said sample,
    wherein said relay system is configured to project said two or more wavelength combs simultaneously onto laterally displaced regions of said sample, and
    wherein said apparatus comprises a spatial sampling element for splitting a beam emitted from said optical source into multiple beamlets, such that said relay system projects multiple sets of said two or more wavelength combs onto a plurality of regions of said sample.

2. The apparatus according to claim 1, wherein the projected multiple sets of two or more wavelength combs form a two-dimensional illumination grid on said sample.

3. The apparatus according to claim 2, wherein said spatial sampling element comprises a two-dimensional lenslet array.

4. The apparatus according to claim 1, wherein said detection system comprises an aperture array for spatially filtering light in said multiple sets of two or more wavelength combs reflected or scattered from said sample.

5. An optical coherence tomography apparatus comprising:
    an optical source for emitting a plurality of wavelengths;
    a wavelength comb generator for generating two or more wavelength combs containing interleaved selections of wavelengths from said plurality of wavelengths;
    a relay system for projecting said two or more wavelength combs onto a sample;
    a detection system for detecting, in a single frame of a two-dimensional sensor array, light in said two or more wavelength combs reflected or scattered from said sample; and
    an optical splitter for splitting light from said optical source into a sample beam and a reference beam, and for recombining said sample and reference beams after said sample beam has interacted with said sample, such that said detection system is able to obtain a tomographic profile of said sample,
    wherein said relay system comprises a wavelength comb selector for projecting said two or more wavelength combs onto said sample sequentially.

6. The apparatus according to claim 5, wherein said wavelength comb selector comprises an adjustable beam steering element and an aperture.

7. The apparatus according to claim 5, wherein said relay system is configured to project said two or more wavelength combs onto the same region of said sample.

8. A method for obtaining a tomographic profile of a sample, said method comprising the steps of:
    splitting light comprising a plurality of wavelengths into a sample beam and a reference beam;
    generating two or more wavelength combs containing interleaved selections of wavelengths from said plurality of wavelengths;
    projecting said two or more wavelength combs onto a sample;
    recombining said sample beam and said reference beam after said sample beam has interacted with said sample;
    detecting, in a single frame of a two-dimensional sensor array, light in said two or more wavelength combs reflected or scattered from said sample; processing the detected light to obtain a tomographic profile of said sample,
    wherein said two or more wavelength combs are projected simultaneously onto laterally displaced regions of said sample, and
    wherein said light comprising a plurality of wavelengths is split into multiple beamlets, such that multiple sets of said two or more wavelength combs are projected onto a plurality of regions of said sample.

9. The method according to claim 8, wherein the projected multiple sets of two or more wavelength combs form a two-dimensional illumination grid on said sample.

10. The method according to claim 8, further comprising the step of:
    scaling the relative phase of a plurality of signals comprising the detected light in said two or more wavelength combs reflected or scattered from said laterally displaced regions of said sample, to account for the different wavelengths in said two or more wavelength combs, to create a synthetic wavefront across said laterally displaced regions of said sample.

11. The method according to claim 10, wherein said scaling also accounts for differences between the distances of said laterally displaced regions from a zero point delay.

12. The method according to claim 10, further comprising the step of applying aberration correction or digital refocusing to said synthetic wavefront, so as to obtain an aberration-corrected image of said laterally displaced regions of said sample.

13. The method according to claim 12, wherein said step of applying aberration correction or digital refocusing comprises the steps of:
    (a) applying a first Fourier transform to said synthetic wavefront;

(b) applying a phase transformation function to account for focus or aberration; and
(c) applying a second Fourier transform.

14. A method for obtaining a tomographic profile of a sample, said method comprising the steps of:
   splitting light comprising a plurality of wavelengths into a sample beam and a reference beam;
   generating two or more wavelength combs containing interleaved selections of wavelengths from said plurality of wavelengths;
   projecting said two or more wavelength combs onto a sample;
   recombining said sample beam and said reference beam after said sample beam has interacted with said sample;
   detecting, in a single frame of a two-dimensional sensor array, light in said two or more wavelength combs reflected or scattered from said sample; and
   processing the detected light to obtain a tomographic profile of said sample,
   wherein said two or more wavelength combs are projected onto said sample sequentially.

15. The method according to claim 14, wherein said two or more wavelength combs are projected onto the same region of said sample.

* * * * *